United States Patent
Tuominen

(10) Patent No.: US 7,120,502 B2
(45) Date of Patent: Oct. 10, 2006

(54) SHAFT CONSTRUCTIONS FOR A MEDICAL DEVICE

(75) Inventor: Scott N. Tuominen, Centerville, MN (US)

(73) Assignee: Medtronic, Inc., Minneapolis, MN (US)

( * ) Notice: Subject to any disclaimer, the term of this patent is extended or adjusted under 35 U.S.C. 154(b) by 384 days.

(21) Appl. No.: 10/371,104

(22) Filed: Feb. 21, 2003

(65) Prior Publication Data

US 2004/0167595 A1 Aug. 26, 2004

(51) Int. Cl.
*A61N 1/00* (2006.01)
(52) U.S. Cl. .................................................. 607/119
(58) Field of Classification Search ................. 607/119, 607/122
See application file for complete search history.

(56) References Cited

U.S. PATENT DOCUMENTS

| | | | | |
|---|---|---|---|---|
| 4,478,898 A | 10/1984 | Kato | | 428/36 |
| 4,717,379 A | 1/1988 | Ekholmer | | 604/43 |
| 5,217,440 A | 6/1993 | Frassica | | |
| 5,330,522 A | 7/1994 | Kreyenhagen | | 607/122 |
| 5,584,873 A | 12/1996 | Shoberg et al. | | |
| 5,593,394 A | 1/1997 | Kanesaka et al. | | 604/282 |
| 5,676,694 A | 10/1997 | Boser et al. | | |
| 5,735,809 A | 4/1998 | Gorsuch | | 604/4 |
| 5,935,159 A | 8/1999 | Cross, Jr. et al. | | |
| 5,957,970 A | 9/1999 | Shoberg et al. | | |
| 6,178,355 B1 | 1/2001 | Williams et al. | | |
| 6,249,708 B1 | 6/2001 | Nelson et al. | | |
| 6,366,807 B1 | 4/2002 | Kosiba et al. | | 604/20 |
| 6,400,992 B1 | 6/2002 | Borgersen et al. | | 607/122 |
| 6,500,167 B1 * | 12/2002 | Webster, Jr. | | 604/528 |
| 6,748,277 B1 * | 6/2004 | Chitre et al. | | 607/122 |
| 2002/0068912 A1 | 6/2002 | Merdan | | 604/264 |

FOREIGN PATENT DOCUMENTS

| | | |
|---|---|---|
| EP | 0 263 645 B1 | 4/1988 |
| EP | 0 266 928 | 5/1988 |
| FR | 2 201 908 | 10/1972 |
| WO | WO 93/05841 | 4/1993 |
| WO | WO 95/32383 | 11/1995 |
| WO | WO 98/51370 | 11/1998 |

* cited by examiner

*Primary Examiner*—Scott M. Getzow
(74) *Attorney, Agent, or Firm*—Carol F. Barry; Girma Wolde-Michael

(57) ABSTRACT

A medical device shaft includes a first longitudinal edge joined to all or a portion of a second longitudinal edge, and an inner surface forming a plurality of lumens separated by a plurality of longitudinal ribs extending along a length of the shaft; wherein a base of each rib is spaced apart from one another and each rib is joined to one another in proximity to a peak of each rib. Each of a plurality of elongated members extends within one of the plurality of lumens of the shaft.

30 Claims, 15 Drawing Sheets

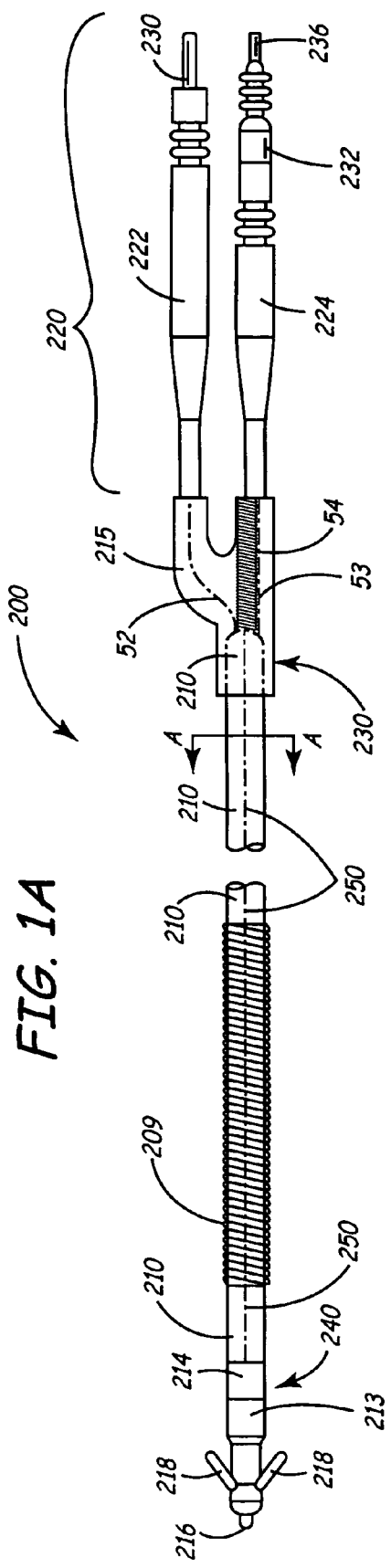

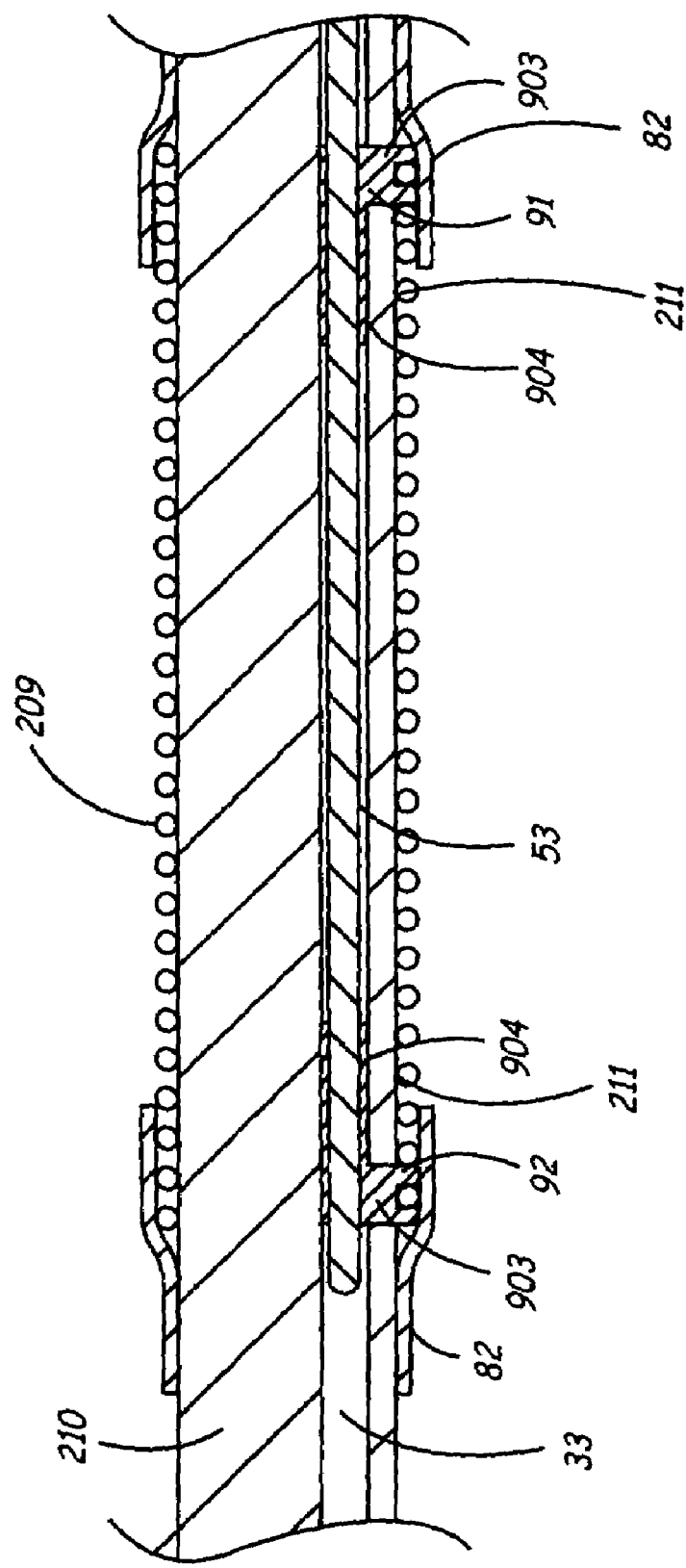

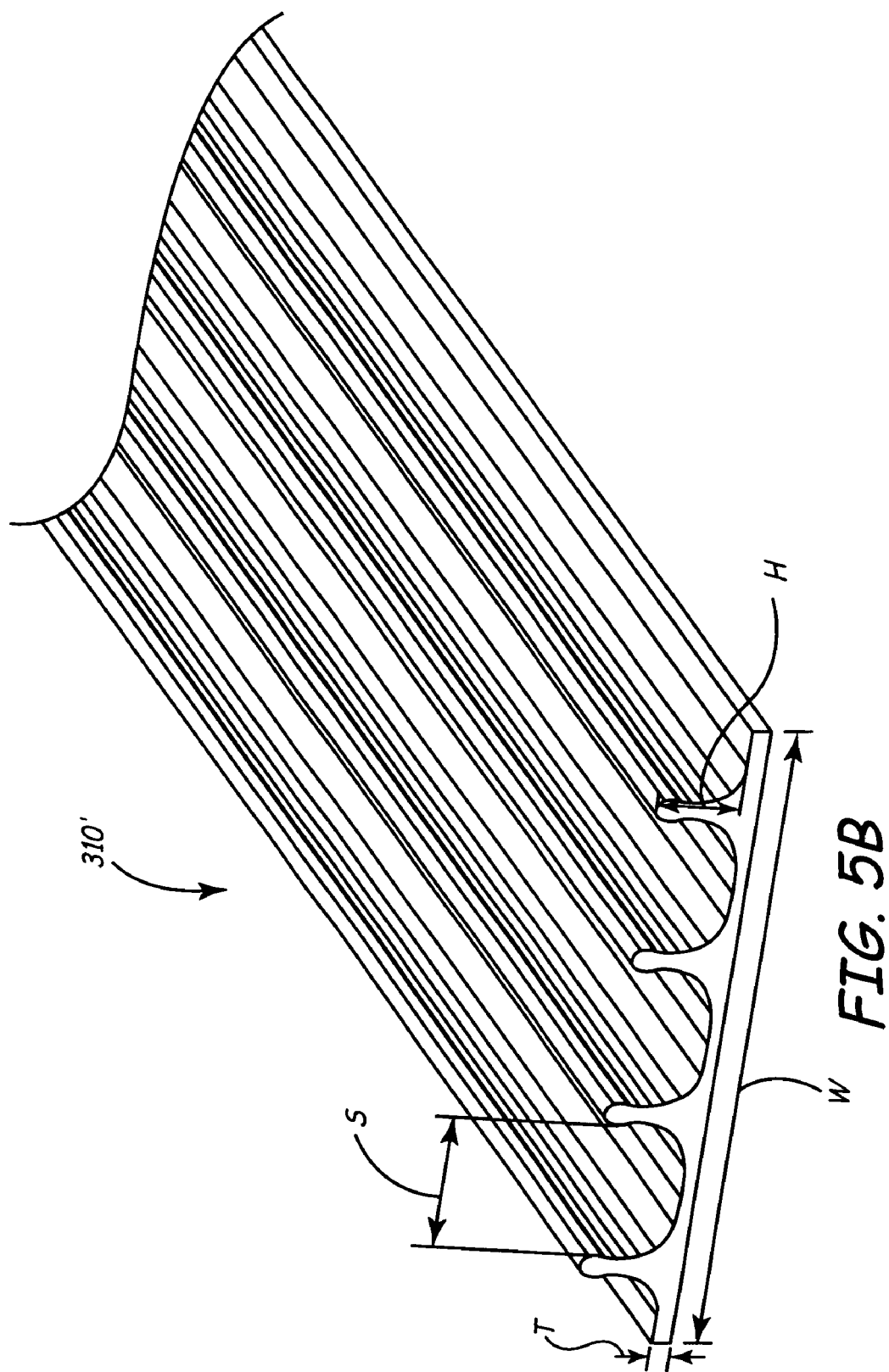

SHAFT CONSTRUCTIONS FOR A MEDICAL DEVICE

FIELD OF THE INVENTION

The present invention is related to medical devices. More specifically, the present invention is related to shaft construction for interventional and implantable medical devices.

BACKGROUND OF THE INVENTION

Medical devices have long utilized generally tubular elongated shafts wherein a distal end of a shaft is inserted within the body of a patient to a target site while a proximal end is manipulated by an operator and, in some cases, joined to an implantable device for delivery of therapy to the site. Such shafts are used in interventional devices, examples of which include infusion catheters, angioplasty catheters, electrical mapping catheters, and ablation catheters; and in conjunction with implantable devices, examples of which include drug infusion pumps, neurological stimulation devices and cardiac monitoring and/or stimulation devices, such as pacemakers and cardioverter defibrillators. Typically, the shafts include one or more elongated members functioning to facilitate diagnosis and/or deliver therapy; examples of such members include electrical conductors, fiber optic bundles, and drug delivery lumens. Additional elongated members are included in some shafts to facilitate steering of the shafts to a specific site within the body; examples of these members include stylet and/or guide wire lumens, pull wires and malleable rods. Embodiments presented herein exemplify a novel shaft construction for medical devices.

DESCRIPTION OF THE DRAWINGS

FIG. 1A is a side view of an implantable electrical lead including a shaft constructed according to one embodiment of the present invention.

FIG. 4E is another section view of an alternate distal portion of the shaft from FIG. 1A, through section line B—B shown in FIG. 2.

FIG. 5B is a perspective view of a sheet from which an alternate embodiment of a medical device shaft is formed.

DETAILED DESCRIPTION OF THE PREFERRED EMBODIMENTS

Figure 1B:
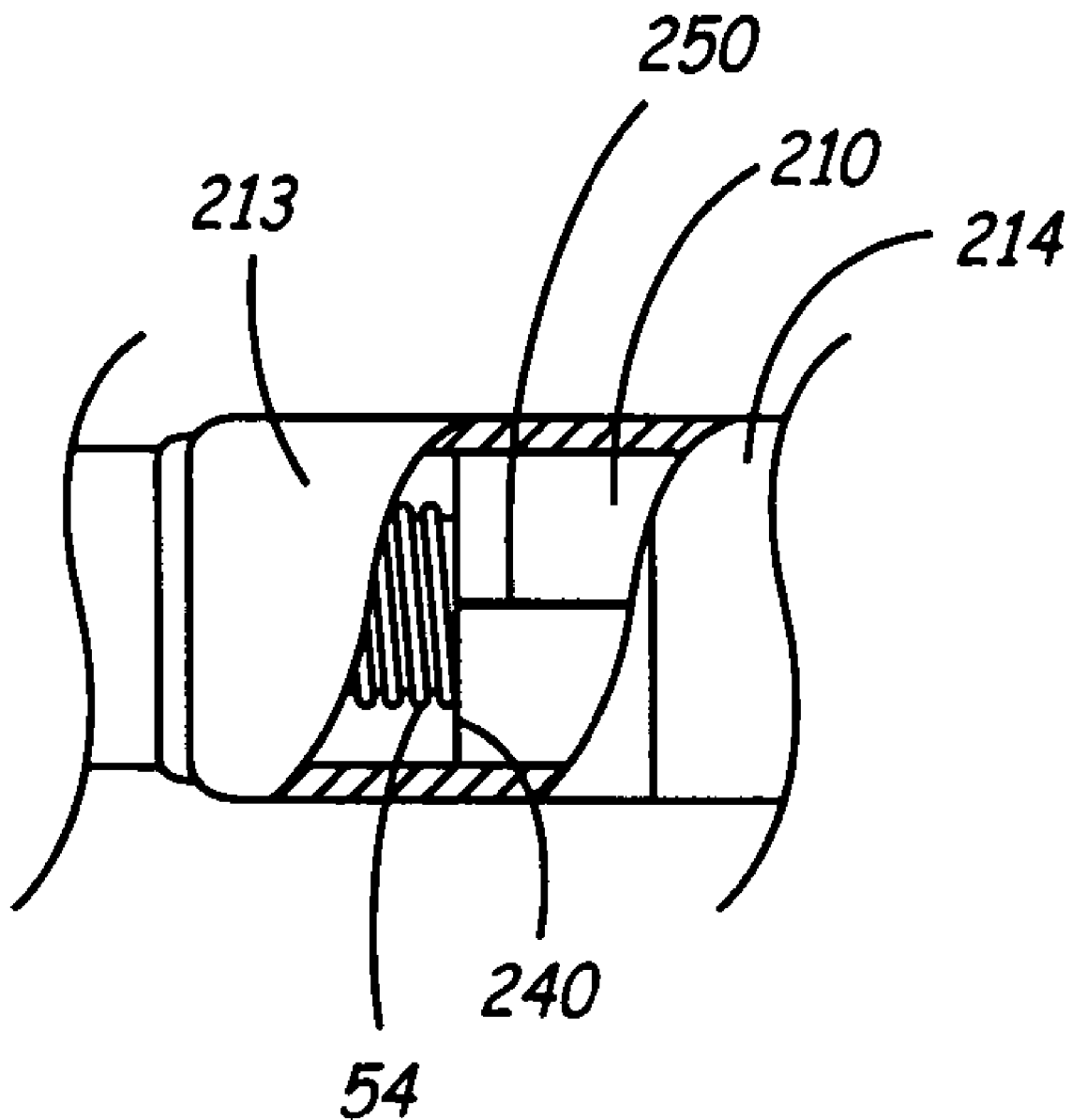
FIG. 1B is a detail view from FIG. 1A with a partial cut-away section view.

FIG. 1A is a side plan view of an implantable electrical lead 200 including a shaft 210 constructed according to one embodiment of the present invention. As illustrated in FIG. 1A, lead 200 further includes a bifurcated connector 220 for connection to an implantable cardioverter defibrillator (not shown), a coil electrode 209, a ring electrode 214 and a tip electrode 216 including a set of tines 218 for fixation within a heart. Electrodes 212, 214, and 216 correspond to any type of electrode known to those skilled in the art of pacing and/or defibrillation lead construction. Bifurcated connector 220 includes a first leg 222 including a high voltage contact 230 to connect coil electrode 209 to the implantable cardioverter defibrillator (ICD) for defibrillation and a second leg 224 including a first low voltage contact 232 and a second low voltage contact 236 to connect ring electrode 214 and tip electrode 216, respectively, to the ICD for pacing and sensing; details of connector configuration, construction, and coupling to implantable devices are well known to those skilled in the art. In an alternate embodiment a single connector leg including contacts for all three electrodes is incorporated in conjunction with shaft 210.

Figure 2:
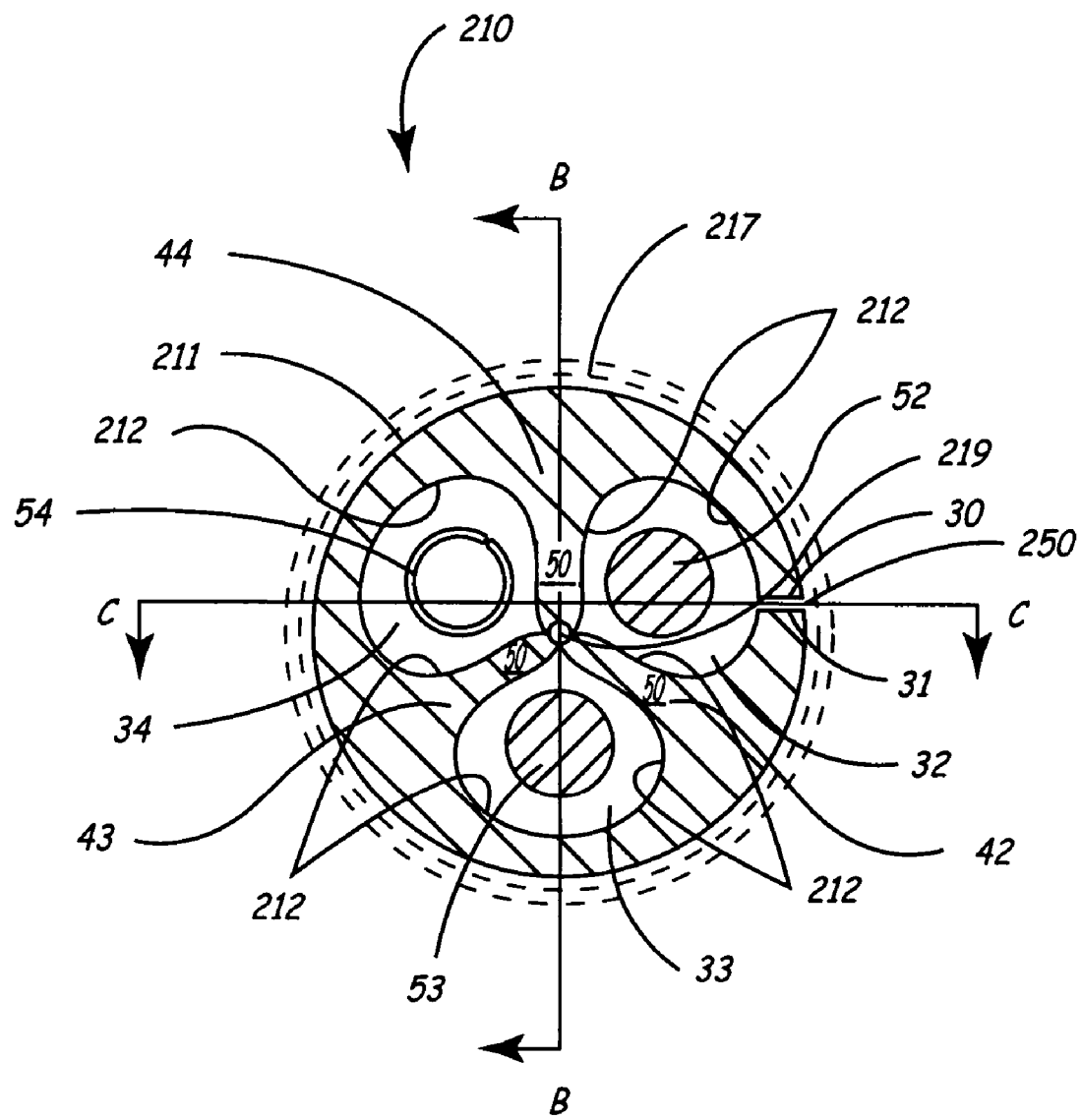
FIG. 2 is a cross-sectional view of the shaft from FIG. 1A through section line A—A.

As further illustrated in FIG. 1A, according to one embodiment, shaft 210 includes a seam 250 and a proximal end 230 of shaft 210 is inserted into a sleeve 215, which joins shaft 210 to bifurcated connector 220, while a distal end 240 of shaft 210 is inserted into an insulative spacer 213 distal to electrode ring 214. Seam 250, according to one embodiment of the present invention, is formed, as illustrated in FIG. 2, where a first longitudinal edge 30 and second longitudinal edge 31 of shaft 210 are joined. According to one embodiment shaft 210 has a substantially round cross-section and an outer diameter between approximately 0.04 inch and 0.160 inch.

Figure 3:
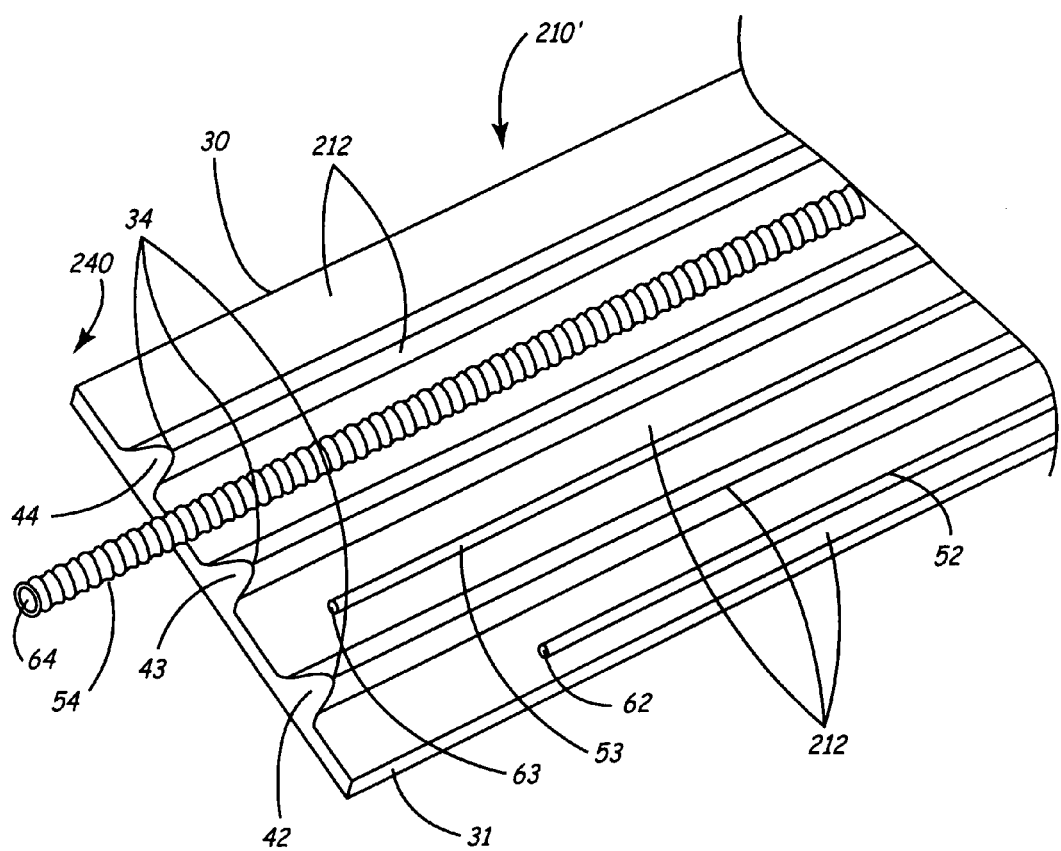
FIG. 3 is a perspective view of a distal portion of a flexible sheet from which the shaft 210 from FIG. 1A is formed according to one embodiment of the present invention.

FIG. 2 is a cross-sectional view of shaft 210 from FIG. 1A through section line A—A. FIG. 3 is a perspective view of a distal portion of a flexible sheet 210' from which shaft 210 is formed according to one embodiment of the present invention. As illustrated in FIG. 2, shaft 210 includes an outer surface 211, an inner surface 212 forming a plurality of lumens 32, 33, and 34 by means of a plurality of ribs 42, 43, and 44, which separate lumens 32, 33, and 34, and a plurality of elongated members 52, 53, and 54 extending within lumens 32, 33, and 34. According to an embodiment of the present invention each elongated member, for example 52, 53, 54, is assembled into shaft 210, as illustrated in FIG. 3. Sheet 210', illustrated in FIG. 3, is formed from a flexible, insulative, biocompatible, and biostable material such as silicone or polyurethane; in one embodiment sheet 210' is formed by extrusion. According to one embodiment of the present invention, as illustrated in FIGS. 2 and 3, first elongated member 52 and second elongated member 53 are cable conductors (designated first cable 52 and second cable 53 from here on) and third elongated member 54 is a coil conductor (designated coil 54 from here on). In various embodiments cables 52, 53 and coil 54 are capable of reliably conducting electrical current after having been subjected to repeated bending and torsional loading imposed by an implant environment; examples of materials from which cables 52, 53 and coil 54 are made include, MP35N alloy, tantalum, and platinum-iridium alloy. An outer diameter of cables 52, 53, ranges between approximately 0.005 inch and approximately 0.025 inch, which, in some embodiments includes an outer layer of insulation formed around cables 52, 53, examples of such insulation including ETFE, PTFE, silicone, and polyurethane. Embodiments include cables constructed according to the methods taught in commonly assigned U.S. Pat. No. 5,760,341, which is incorporated herein in its entirety. An outer diameter of coil 54 ranges from approximately 0.005 inch to approximately 0.060 inch depending upon a diameter of wire from which coil is formed and a desired inner diameter of coil for various embodiments. Coil 54 further includes one wire or multiples wires, up to approximately six, according to various embodiments.

Figure 7A:
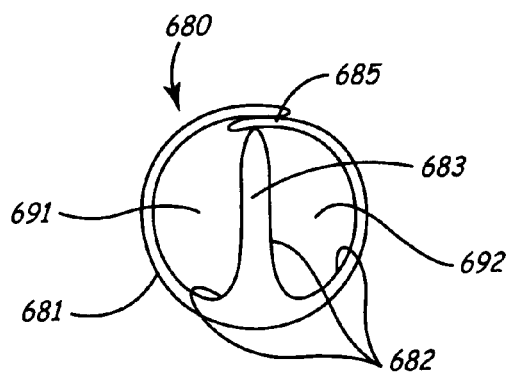
FIGS. 7A–B are cross-sectional views of alternate embodiments of a dual lumen shaft.
Figure 7B:
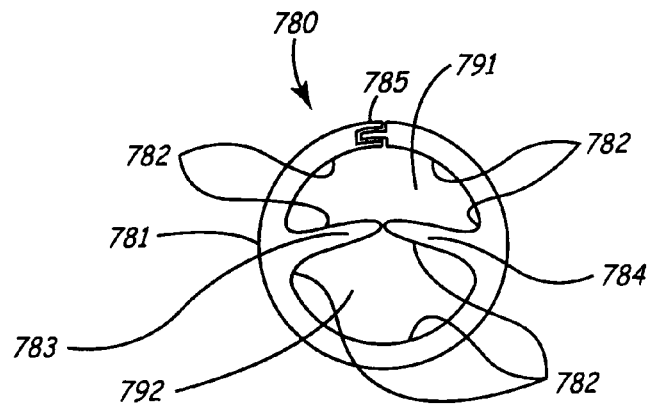

As illustrated in FIG. 3, first cable 52, second cable 53, and coil 54 are each disposed on inner surface 212 of flexible sheet 210' alongside ribs 42, 43, and 44, respectively, prior to rolling sheet 210' such that first longitudinal edge 30 meets with second longitudinal edge 31 to form shaft 210 shown in FIGS. 1 and 2. According to embodiments of the present invention first edge 30 is joined by solvent welding or an adhesive bond, for example a silicone medical adhesive bond, to second edge 31 in a butt joint forming seam 250, as illustrated in FIG. 2. Alternate embodiments include seams formed by a lap joint and by a tongue-in-groove joint, as illustrated in FIGS. 7A–B.

Additional embodiments include an outer sheath 217, illustrated with phantom lines in FIG. 2, which is formed about outer surface 211 of shaft 210. In alternate embodiments sheath 217 is formed from flexible, biocompatible, and biostable tubing made from materials including, but not limited to silicone, polyurethane, ETFE, PTFE, and e-PTFE. In one embodiment seam 250 is welded or bonded prior placing sheath 217 about shaft 210 while, in another embodiment, seam is welded or bonded after sheath 217 is placed about shaft 210. Furthermore, in another embodiment, longitudinal edges, such as edges 30, 31 do not meet so that a sheath, such as sheath 217, is an integral member in creating a seam between the edges, by either bringing the edges together or filling a gap between the edges. Alternate embodiments include an interference fit of sheath 217 on shaft 210, a line-to-line fit of sheath 217 on shaft 210, or a gap between sheath 217 and shaft 210. In another embodiment, sheath 217 may be re-flowed, according to methods known to those skilled in the art, about shaft 210 in order to seal seam 250 without adhesive; a polyurethane material is one example of a material from which sheath 217 may be formed for re-flow. In yet another set of embodiments, outer sheath 217 is in the form of a coil, the coil composed of a polymer or metal material.

Ribs 42, 43, and 44 include peaks 50, which as illustrated in FIG. 2, come together in proximity to a central longitudinal axis 219 of shaft 210 to form lumens 32, 33, 34. Ribs 42, 43, and 44, in some embodiments, are dimensioned such that lumens 32, 33, and 34 are formed to accommodate diameters of elongated members, such as cables 52 and 53 and coil 54, in a slightly looser than line-to-line fit. An adhesive bond is formed between ribs along an entire length of axis 219 in one embodiment; in other embodiments adhesive bonds are formed at selected, discrete locations along axis 219. Additional embodiments, to be described in conjunction with FIGS. 8A–B, include ribs joined to a central core 820, 920.

As further illustrated in FIG. 3, according to one embodiment, distal ends 62, 63, and 64 of first cable 52, second cable 53, and coil 54, respectively, are positioned with respect to distal end 240 of sheet 210' to correspond with locations of electrodes 212, 214, and 216, respectively, prior to rolling sheet 210' in shaft 210. Means, according to several embodiments, for coupling cables 52 and 53 to electrodes 212 and 214 are described in conjunction with FIGS. 4A–D.

Referring back to FIG. 1A, first cable 52, extending from contact 230 is coupled to coil electrode 209, second cable 53, extending from contact 232, is coupled to ring electrode 214, and coil 54, extending from contact 236, is coupled to tip electrode 216. Phantom lines show proximal end 230 of shaft 210 within sleeve 215, first cable 52 traversing from first connector leg 222 into shaft 210 and second cable 53 and coil 54 traversing from second connector leg 224 into shaft 210. FIG. 1B, a detail view from FIG. 1A with a partial cut-away section view through insulative spacer 213, shows distal end 240 of shaft 210 extending through electrode ring 214 and into insulative spacer 213 where coil 54 exits shaft 210 to couple with electrode tip 216. Methods and materials used to construct an assembly of electrode tip 216, tines 218, and insulative spacer 213 along with means for joining the assembly to shaft 210 and coupling coil 54 to electrode tip 216 are all known to those skilled in the art of lead construction.

Figure 4A:
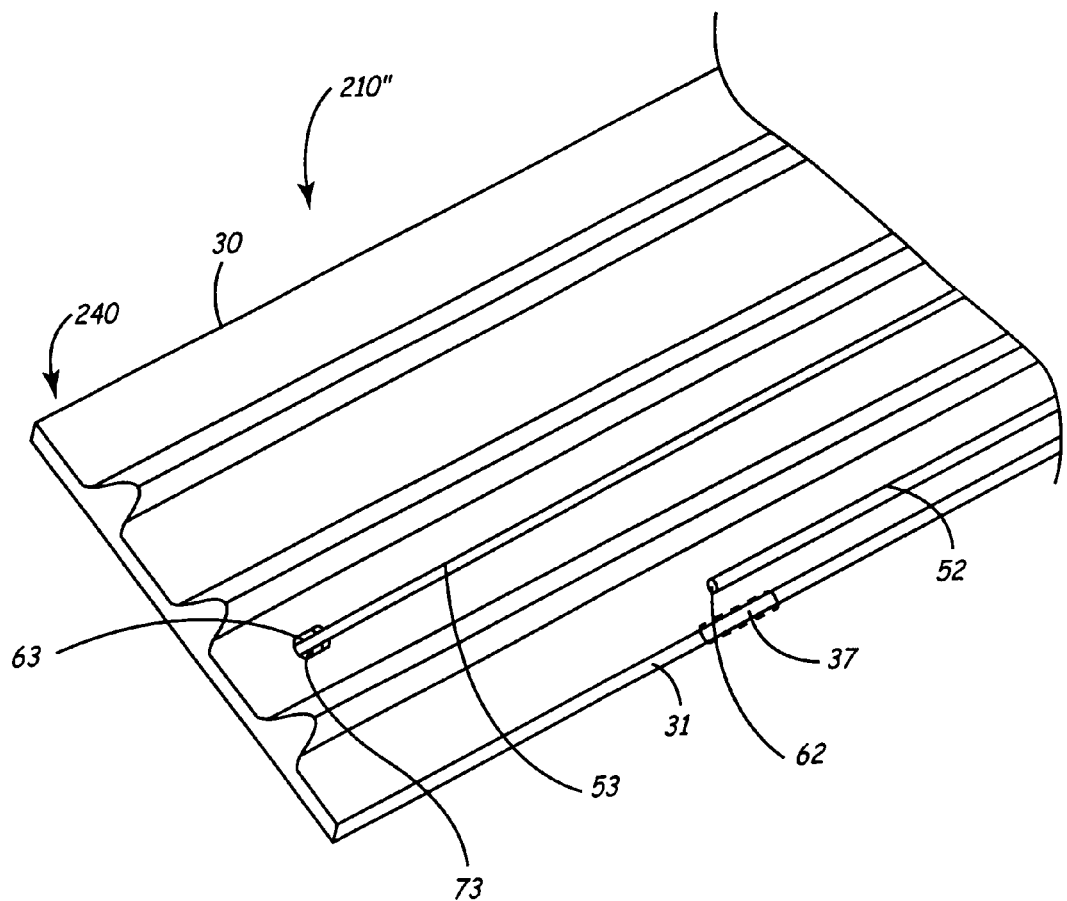
FIG. 4A is a perspective view of a flexible sheet including a hole.
Figure 4B:
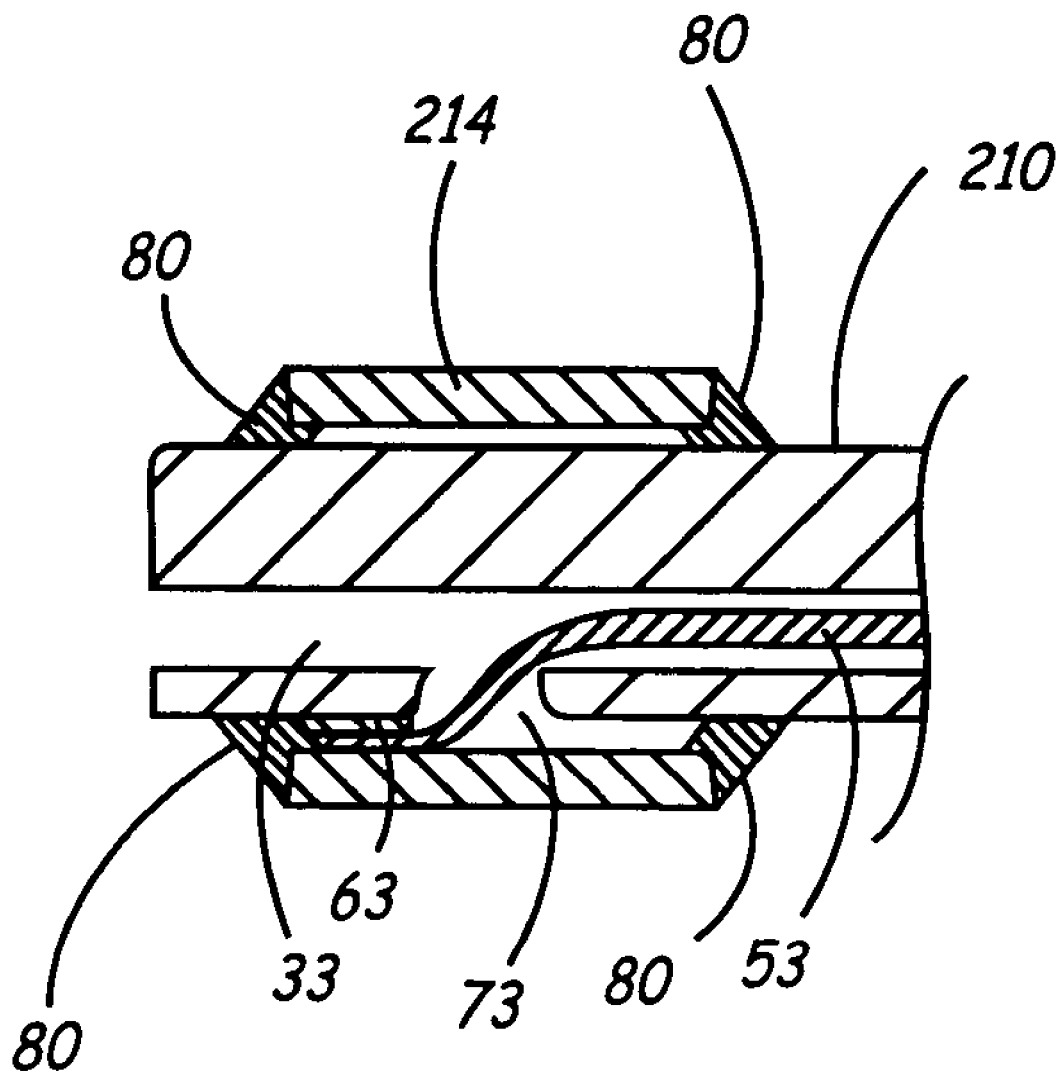
FIG. 4B is a section view of a distal portion of the shaft from FIG. 1A, through section line B—B shown in FIG. 2.
Figure 4C:
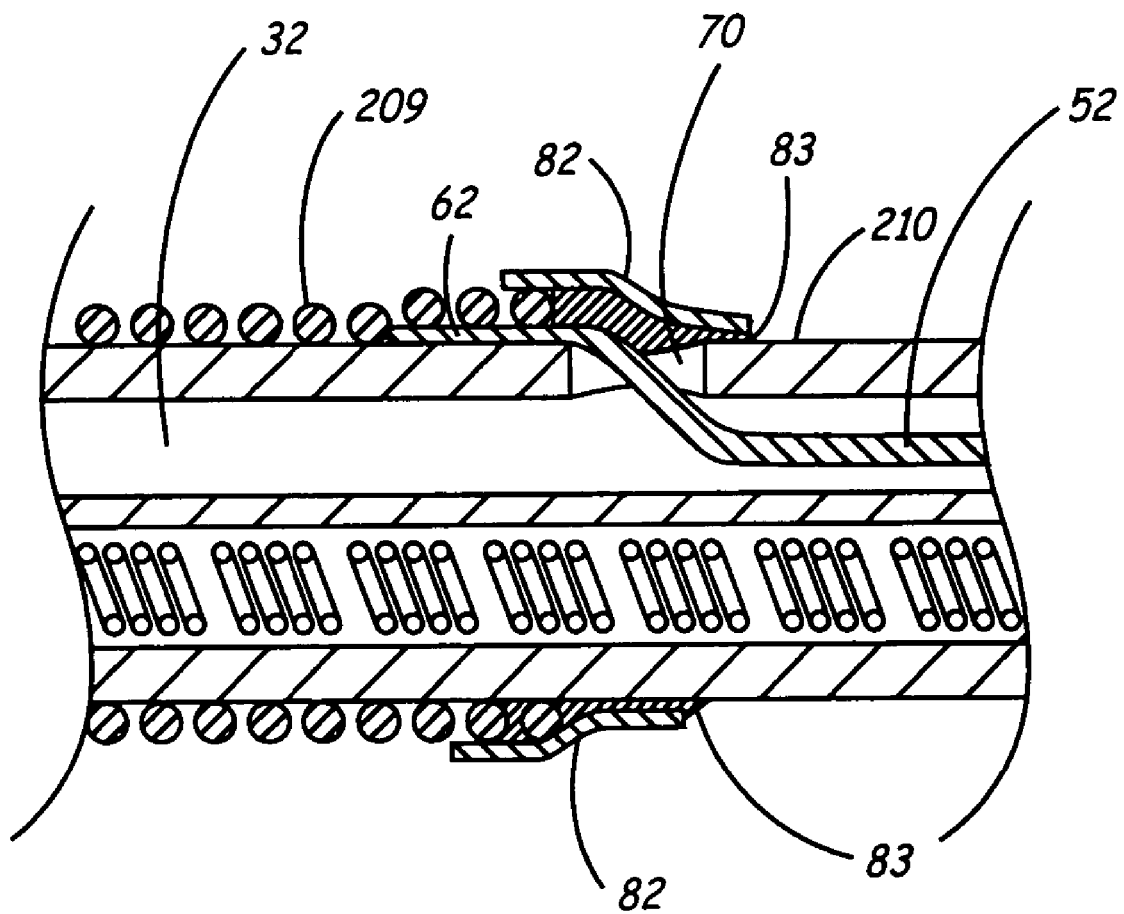
FIG. 4C is a section view of a distal portion of the shaft from FIG. 1A, through section line C—C shown in FIG. 2.

FIG. 4A is a perspective view of a flexible sheet 210" including a hole 73 through which distal end 63 of cable 53 passes. In embodiments of the present invention, hole 73 is punched or cut out of sheet 210' prior to laying cables 52, 53 and coil 54 along inner surface 212. As illustrated in FIG. 4A hole 73 is located in proximity to distal end 240, which, once sheet 210" is rolled into shaft 210, as illustrated in FIG. 4B, will be inserted within ring electrode 214 so that distal end 63 of cable 53 can be coupled to ring electrode 214. As is further illustrated in FIG. 4A, distal end 62 of first cable 52 is positioned in proximity to a location 37, indicated by phantom lines along edge 31, where a gap 70 (FIG. 4C) in seam 250 will be formed. FIG. 4C illustrates distal end 62 of cable 52 passing through gap 70 to couple with coil electrode 209.

FIG. 4B is a section view of a distal portion of shaft 210 in proximity to ring electrode 214, through section line B—B (FIG. 2), wherein second cable 53, exiting through hole 73 is coupled with ring electrode 214. According to embodiments of the present invention second cable 53 is coupled to ring electrode 214 by means of crimping, staking or welding using methods well known to those skilled in the art of lead construction. According to one embodiment a backfill of medical adhesive 80 is used to seal lumen 33 in proximity to hole 73 after second cable 53 is coupled to ring electrode 214.

FIG. 4C is a section view of a distal portion of shaft 210, in proximity to coil electrode 209, through section line C—C (FIG. 2), wherein first cable 52 exiting through gap 70 in seam 250 is coupled to coil electrode 209 according to crimping or welding techniques known to those skilled in the art. FIG. 4C further illustrates gap 70 sealed with a tubing band 82 over a medical adhesive backfill 83 according to one embodiment of the present invention.

Figure 4D:
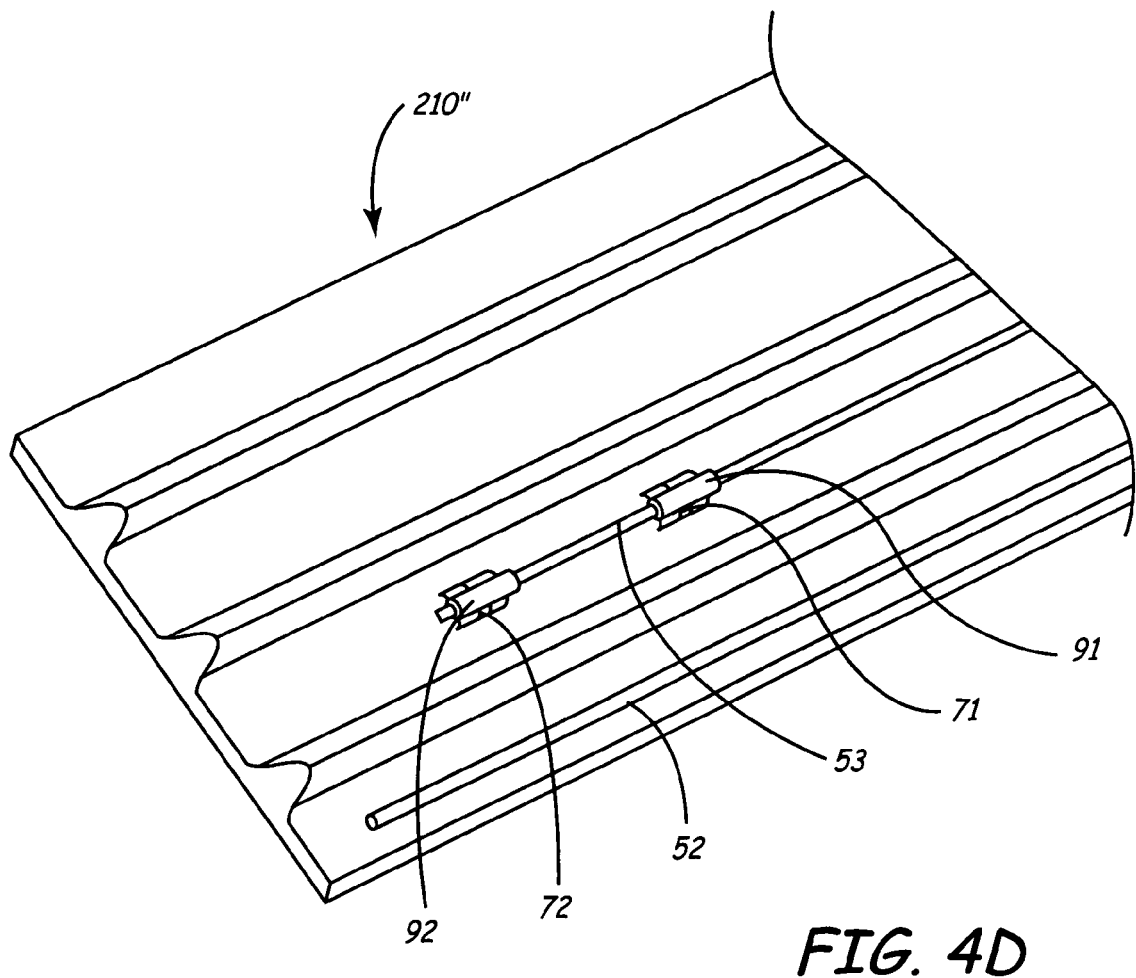
FIG. 4D is a perspective view of a sheet including a first hole and a second hole.

FIG. 4D is a perspective view of a sheet 210''' including a first hole 71 and a second hole 72. As illustrated in FIG. 4D, according to an alternate embodiment, second cable 53 is positioned on sheet 210''' for coupling with coil electrode 209 (FIG. 1) in two places, while first cable 52 is positioned for coupling to ring electrode 214 through a gap in seam 250, such as gap 70 described in conjunction with FIGS. 4A and C. FIG. 4D further illustrates a first conductive sleeve 91 and a second conductive sleeve 92 included to facilitate coupling second cable 53 to coil electrode 209. Various embodiments of such sleeves are described in commonly assigned U.S. Pat. No. 5,676,694, incorporated herein by reference in its entirety. FIG. 4E illustrates an embodiment utilizing one type of sleeve described in the '694 patent.

FIG. 4E is a section view of a distal portion of shaft 210 in proximity to coil electrode 209 through section line B—B (FIG. 2), wherein first and second sleeves 91, 92 each include a barrel portion 904, crimped to cable 53 and a tower portion 903, passing through holes 71 and 72. Coil electrode 209 is welded to each tower portion 903 protruding from outer surface 211 of shaft 210. In alternate embodiments, a single sleeve, disposed at a hole or a gap in a seam, is incorporated for a single coupling of a cable to a coil or ring electrode, such as coil electrode 209 or to ring electrode 214.

Figure 5A:
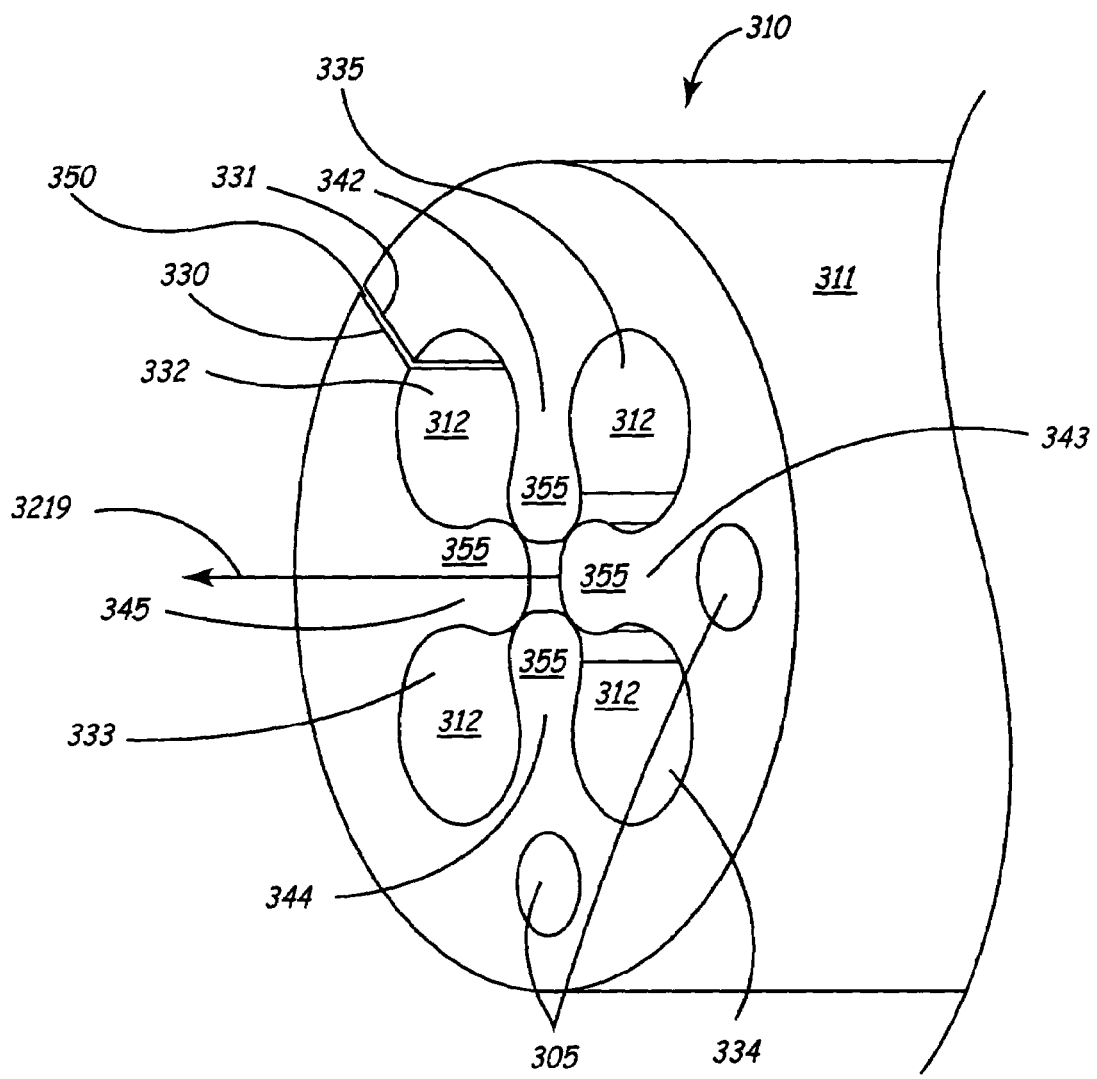
FIG. 5A is a perspective view of an axial cross-section of an alternate embodiment of a medical device shaft.

FIG. 5A is a perspective view of an axial cross-section of an alternate embodiment of a medical device shaft 310 formed from an extruded sheet. FIG. 5B is a perspective view of a sheet 310' from which a medical device shaft, such as shaft 310, is formed. FIG. 5A illustrates shaft 310 including a seam 350, formed by a first longitudinal edge 330 and a second longitudinal edge 331, an outer surface 311, and an inner surface 312 forming a plurality of lumens 332, 333, 334, and 335 by means of a plurality of ribs 342, 343, 344, and 345, which separate lumens 332, 333, 334 and 335. Ribs 342, 343, 344 and 345 include peaks 355, which as illustrated in FIG. 5, come together in proximity to a central longitudinal axis 3219 of shaft 310. An adhesive bond is formed between ribs along an entire length of axis 3219 in one embodiment; in other embodiments adhesive bonds are formed at selected, discrete locations along axis 3219. As will be described in conjunction with FIGS. 8A–B, a central core is included in alternate embodiments.

FIG. 5B illustrates sheet 310' including a width "W", a rib height "H", a rib spacing "S", and a thickness "T" alongside ribs. According to embodiments of the present invention, width "W" of sheet is determined according to a desired outer diameter of a resulting shaft, being approximately equal to a circumference of the shaft, while rib height "H" and spacing "S" depend upon the number of ribs and a desired lumen size. A spacing of ribs is uniform, as illustrated in FIG. 5B, or variable according to a combination of lumen sizes desired in the resultant shaft. Thickness "T" is determined according to functional requirements of the resulting shaft and is in a range between approximately 0.005 inch and 0.020 inch. Three examples according to the present invention are as follows:

For a shaft including three ribs and an outer diameter≈0.042 inch, W≈0.132 inch, H≈0.013 inch, S≈0.039 inch, and T≈0.005 inch;

For a shaft including four ribs and an outer diameter≈0.048 inch, W≈0.151 inch, H≈0.015 inch, S≈0.033 inch, and T≈0.005 inch; and For a shaft including four ribs and an outer diameter≈0.055 inch, W≈0.173 inch, H≈0.020 inch, S≈0.030 inch, and T≈0.005 inch.

Although not shown in FIGS. 5A–B, embodiments of the present invention further include one or more elongated members, each extending within a lumen. In alternate shaft embodiments, depending upon the type of medical device, elongated members include not only electrical conductors such as cables 52, 53 and coil 54, but also fiber optic bundles, malleable rods and pull wires.

FIG. 5A further illustrates shaft 310 including compression lumens 305 extending longitudinally along the shaft wall on either side of lumen 334, according to one embodiment of the present invention. Commonly assigned U.S. Pat. No. 5,584,873, incorporated herein in its entirety, describes compression lumens formed in lead bodies to protect conductors from crushing forces; therefore, a coil conductor, for example, extending through lumen 334 is likewise protected within in shaft 310 according to one embodiment of the present invention.

In further alternate embodiments any of the lumens are left empty to facilitate infusion of a material, inflation of a balloon member, and/or to provide passage for stylet and/or guide wire delivery; in some embodiments a liner or hollow tube is provided within one or more lumen for these applications. Furthermore it is contemplated that more than one elongated member are disposed within a single lumen of an alternate embodiment.

Figure 6A:
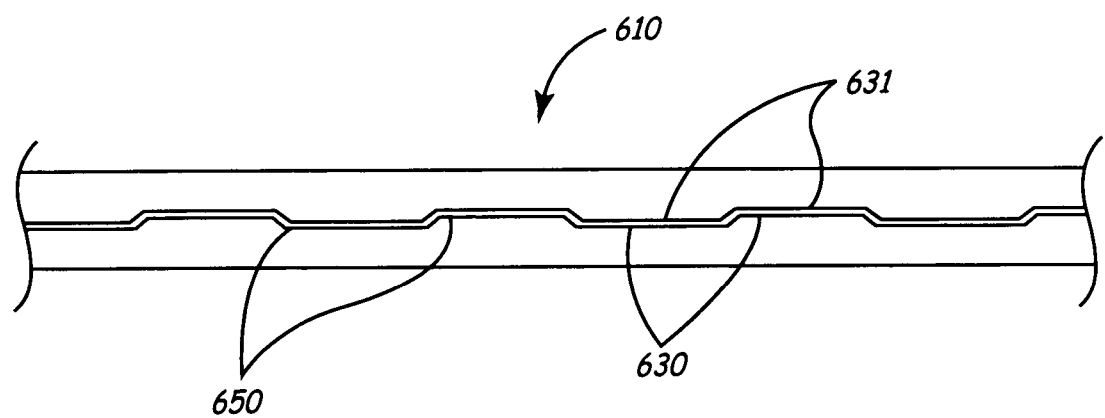
FIGS. 6A–B are plan views of a portion of alternate embodiments of a shaft.

FIGS. 6A–B and 7A–B illustrate alternate embodiments of seams included in shafts according to the present invention. FIG. 6A plan view of a portion of a shaft 610 formed from a sheet including interlocking features along longitudinal edges. FIG. 6A illustrates a seam 650 formed between a first longitudinal edge 630 and a second longitudinal edge 631 wherein edges 630 and 631 interlock. In one embodiment, as illustrated in FIG. 6A, interlocking features of edges 630, 631 are macroscopic in size while in another embodiment microscopic interlocking features are incorporated.

Figure 6B:
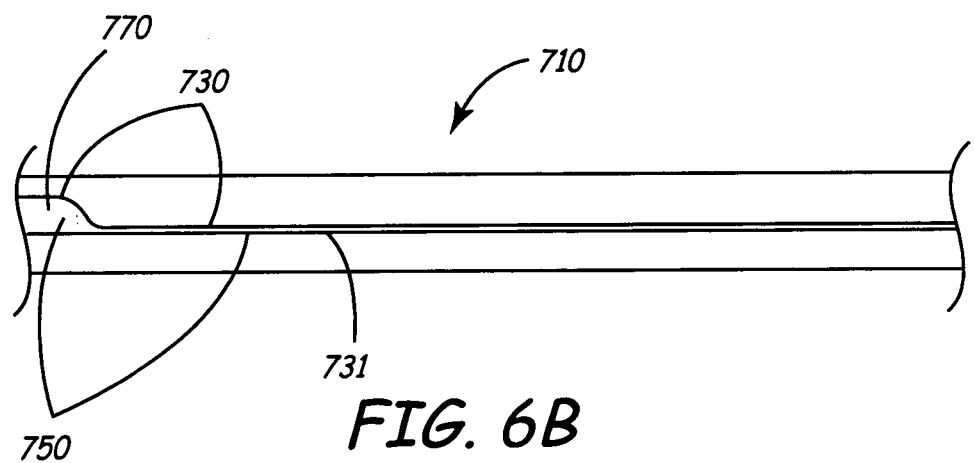

FIG. 6B is a plan view of a portion of a shaft 710 including a seam having a separated edge. FIG. 6B illustrates a hole 770 formed in a seam 750 where a first edge 730 separates from a second edge 731. According to some embodiments hole 770 is disposed along a proximal portion of shaft 710 to be utilized as a port for a guide wire or a stylet used to deliver shaft 710 to a target site, while, in other embodiments, hole 770 is disposed along a distal portion of shaft 710 to be utilized as a port for infusion of a material or for passage of an elongate element outside shaft to join with an external member, for example cable 53 coupled to coil electrode 209 shown in FIG. 4C.

FIG. 7A is a cross-sectional view of a dual lumen shaft 680. According to one embodiment of the present invention, FIG. 7A illustrates a seam 685 formed by means of a lap joint. FIG. 7A further illustrates shaft 680, formed from a sheet, including an outer surface 681, an inner surface 682 forming a first lumen 691 and a second lumen 692, and a single rib 683 separating first lumen 691 from second lumen 692.

FIG. 7B is a cross-sectional view of another dual lumen shaft 780. According to one embodiment, FIG. 7B illustrates a seam 785 formed by means of a tongue-in-groove joint. FIG. 7B further illustrates shaft 780, formed from a sheet, including an outer surface 781, an inner surface 782, forming a first lumen 791 and a second lumen 792, and a first rib 783 and a second rib 784; wherein first and second ribs 783, 784 separate first and second lumens 791, 792.

Figure 8A:
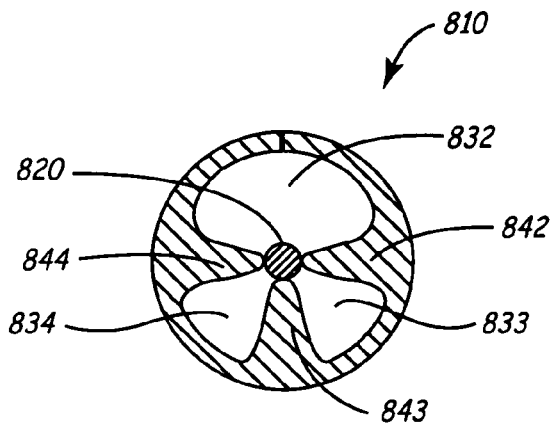
FIG. 8A is a cross-sectional view of a tri-lumen shaft including a core.
Figure 8B:
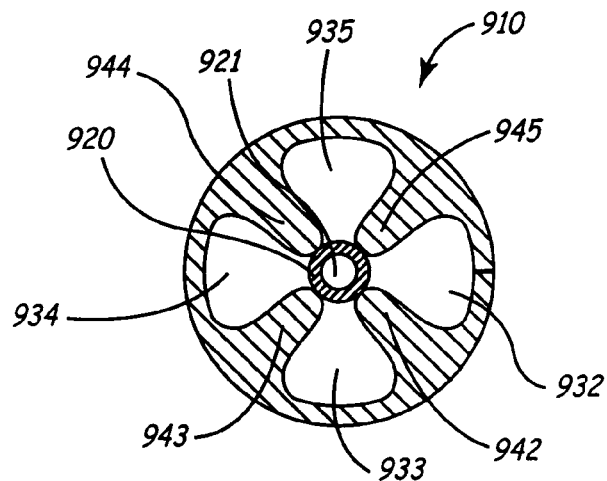
FIG. 8B is a cross-sectional view of a four-lumen shaft including a core.

FIGS. 8A–B illustrate alternate embodiments of shafts including central cores. FIG. 8A is a cross-sectional view of a tri-lumen shaft 810 including a solid core 820. According to one embodiment, FIG. 8A illustrates shaft 810, formed from a sheet rolled about core 820 and including ribs 842, 843, 844 separating lumens 832, 833, 834 and joined to core 820 by means of an adhesive bond or solvent welding. In alternate embodiments core 820 is made of a malleable material such that shaft 810 can be preformed for delivery.

FIG. 8B is a section view of an alternate embodiment of a shaft 910 including a hollow core 920. According to one embodiment, FIG. 8B illustrates shaft 910, formed from a sheet rolled about hollow core 920 and including ribs 942, 943, 944, 945 separating lumens 932, 933, 934, 935 and joined to core 920 by means of an adhesive bond or solvent welding. In alternate embodiments a lumen 921 of core 920 is used for infusion of materials, inflation of a balloon member, or passage of a guide wire and/or stylet.

Although not shown in FIGS. 7A–B and 8A–B, shafts according to these embodiments include one or more elongated members, each extending within a lumen. In alternate shaft embodiments, depending upon the type of medical device, elongated members include electrical conductors, fiber optic bundles, malleable rods and pull wires.

Figure 9:
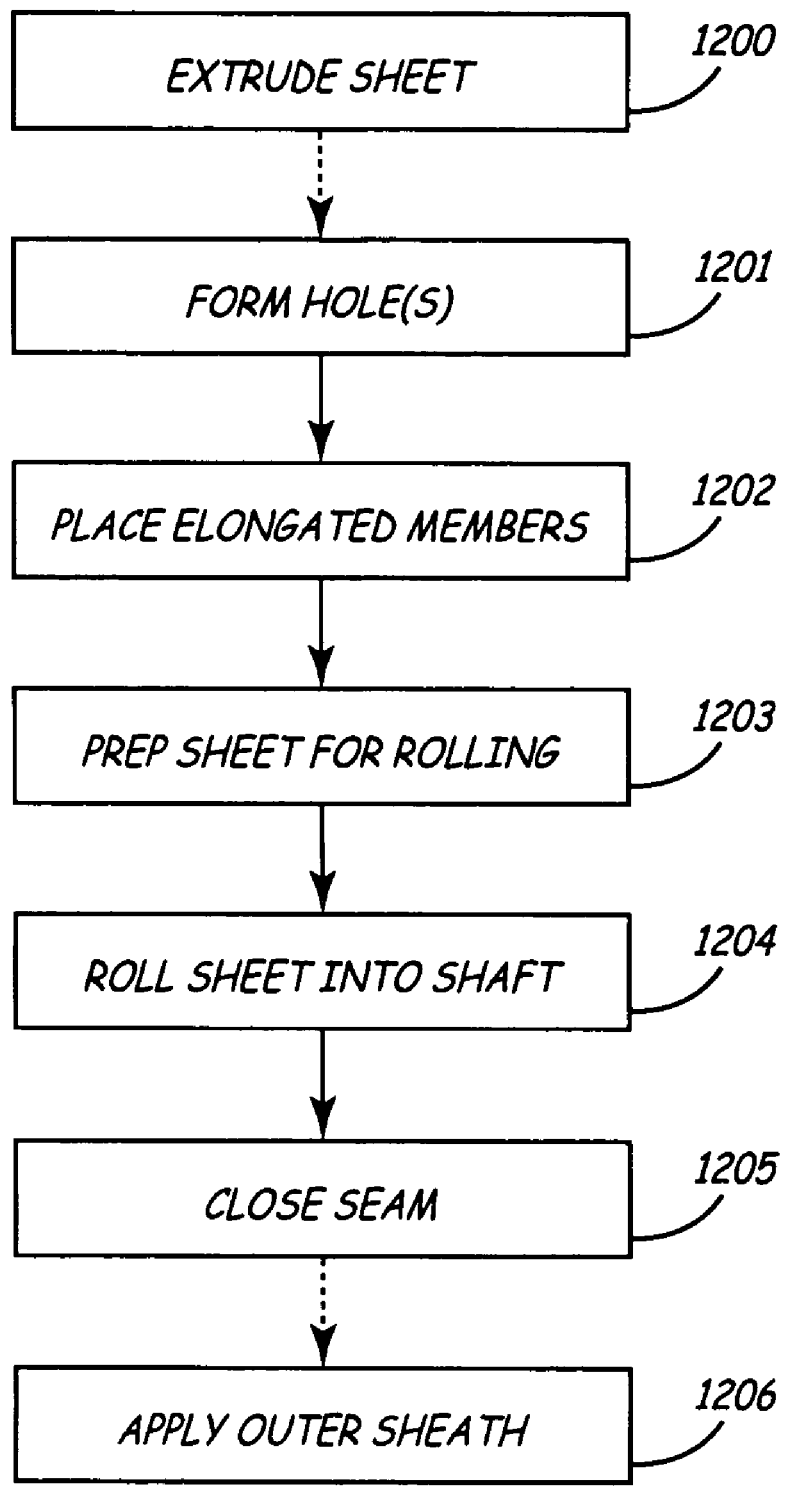
FIG. 9 is a flow chart outlining assembly methods for a medical device shaft.

FIG. 9 is a flow chart outlining assembly methods for a medical device shaft. According to embodiments of the present invention, a sheet including a plurality of longitudinal ribs formed along a surface is extruded (1200) having length and width dimensions corresponding to a desired length and diameter, respectively, of a shaft to be formed from the sheet; and having a height, spacing and number of ribs corresponding to sizes and a number of lumens desired in the resultant shaft. According to alternate embodiments materials from which a sheet is extruded include silicone, polyurethane, polyether block amides, polypropylene, and polyethylene; the material selection dependent upon the application of the sheet as either part of a permanently implantable medical device or a disposable interventional medical device. Optionally, one or more holes are formed (1201) through a wall of the sheet in between the ribs. In alternate embodiments holes formed in the sheet serve a variety of purposes, for example as infusion ports from a lumen of the resultant shaft or as a passageway for joining an elongated member extending within a lumen of the shaft to another member outside the shaft. One or more elongated members are placed on the surface of the shaft (1202), each alongside a rib. The types of elongated members have been previously described and depend upon the function of the medical device into which the resultant shaft will be integrated. A distal end of each member is positioned according a location corresponding to a junction with another member of the medical device to which the elongated member will be joined when the shaft is integrated into the medical device. In some embodiments, as previously described, a portion of an elongated member may be inserted through a hole, formed in the sheet, for a junction along the opposite surface of the sheet, which forms the outer surface of the resultant shaft. After placing the elongated members, the sheet is prepped for rolling (1203). According to various embodiments prepping includes application of adhesive to the ribs of the sheet and fixing all or a portion of the elongated members to the surface of the sheet. Applying adhesive to the ribs prepares for a bond to be formed between the ribs, when the sheet is rolled into a shaft (1204), so that the resultant lumens of the shaft are isolated from one another. Alternately adhesive may be injected down the center of the resultant shaft after the sheet is rolled. Fixing all or a portion of the elongated members to the surface of the sheet may help to hold the members in position as the shaft is being rolled; in some embodiments the fixation is designed to be temporary, only to facilitate the rolling process, while in other embodiments the fixation is designed to be permanent. In additional embodiments prepping the sheet for rolling includes placing a longitudinal core a length of the sheet around which the sheet will be rolled (1204) to form a shaft; the core is either removed from the resultant shaft, being used only to facilitate rolling, or the core is a permanent structure, centrally located within the shaft and to which the ribs are joined. When the sheet is rolled, two longitudinal edges of the sheet come together to form a seam, which may be closed (1205) by various means. According to alternate embodiments, means to seal the seam include an adhesive bond, a solvent weld, and a material re-flow. In one embodiment a sheet formed of a silicone includes a seam sealed by a silicone medical adhesive bond; in an alternate embodiment a sheet formed of a polyurethane includes a seam sealed by either a polyurethane bond, a solvent weld, or a thermally induced material re-flow. In other embodiments all or a portion of the longitudinal edges don't come together when the shaft is rolled; in one case a discrete gap is desired to create hole for communication between the inner surface and outer surface of the shaft; in another case a filler is utilized to fill the gap along the entire length of the edges. Optionally, a final step in assembling a shaft includes applying an outer sheath around the shaft (1206). According to one method, outer sheath, in a sheet or tape form, is wrapped around a shaft while by another method outer sheath, in a tubular form is slid over the shaft; in the latter case a solvent such as isopropyl alcohol or heptane may be used to swell the sheath for assembly. According to one embodiment, an outer sheath is shrunk and/or re-flowed around a shaft to help seal a seam; in another embodiment an outer sheath is a line-to-line fit around a shaft; and in yet another embodiment a gap is held between an outer sheath and a shaft.

Finally, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

The invention claimed is:

1. A medical device comprising a shaft, the shaft comprising:
    a rolled sheet of flexible material having a first longitudinal edge, a second longitudinal edge, and a sheet surface between the first and second longitudinal edges that forms an inner shaft surface,
    the first and second longitudinal edges of the sheet being joined in abutment to form a seam extending along a length of the shaft,
    the sheet surface including a plurality of longitudinal ribs such that the rolled sheet forms a plurality of lumens within the shaft with the ribs separating the plurality of lumens from one another; and
    a plurality of elongated members, each of the plurality of members extending within one of the plurality of lumens;
    wherein all or a portion of the first longitudinal edge joins to the second longitudinal edge in a single seam;
    each of the longitudinal ribs include a base and a peak;
    the base of each of the plurality of ribs are spaced apart from one another; and
    the plurality of ribs join to one another in proximity to their peaks.

2. The medical device of claim 1, wherein one of the plurality of elongated members is a member of the group comprising an electrical conductor coil and an electrical conductor cable.

3. The medical device of claim 2, wherein one of the plurality of elongated members is a coil conductor and the shaft further comprises a first compression lumen, a second compression lumen, and an outer surface extending along the length of the shaft and forming a wall with the inner surface; wherein the first and second compression lumens extend along the length within the wall in proximity to the coil conductor.

4. The medical device of claim 1, wherein one of the plurality of elongated members is a member of the group consisting of a pull wire and a malleable rod.

5. The medical device of claim 1, wherein one of the plurality of elongated members is fiber optic bundle.

6. The medical device of claim 1, further comprising an outer sheath extending along all or a portion of the length of the shaft and forming all or a portion of an outer surface of the shaft.

7. The medical device of claim 1, wherein the shaft further comprises an outer surface extending along the length of the shaft and forming a wall with the inner surface and a plurality of holes formed through wall providing communication between one or more of the plurality of lumens and an area exterior to the shaft.

8. The medical device of claim 7, further comprising an electrode formed about the outer surface of the shaft and wherein the plurality of elongated members includes a conductor, the conductor coupled to the electrode at a first location via a first hole of the plurality of holes.

9. The medical device of claim 8, wherein the conductor is further coupled to the electrode at a second location via a second hole of the plurality of holes.

10. The medical device of claim 1, wherein the first longitudinal edge of the shaft joins to the second longitudinal edge by means of an adhesive bond, a solvent weld, or material re-flow.

11. The medical device of claim 1, wherein the first longitudinal edge of the shaft joins to the second longitudinal edge in a lap joint.

12. The medical device of claim 1, wherein the first longitudinal edge of the shaft joins to the second longitudinal edge in a bull joint.

13. The medical device of claim 1, wherein the first longitudinal edge of the shaft joins to the second longitudinal edge in a tongue-in-groove joint.

14. The medical device of claim 1, wherein the shaft further comprises a central core disposed along the length and wherein the each of the plurality of ribs includes a peak; wherein each of the peaks of the plurality of ribs join to the core.

15. The medical device of claim 14, wherein the central core of the shaft is hollow.

16. The medical device of claim 1, wherein the plurality of lumens includes a first lumen and a second lumen and the plurality of ribs includes a first rib and a second rib.

17. The medical device of claim 16, wherein the plurality of lumens further includes a third lumen and the plurality of ribs further includes a third rib.

18. The medical device of claim 17, wherein the plurality of lumens further includes a fourth lumen and the plurality of ribs includes a fourth rib.

19. A medical device comprising a shaft, the shaft comprising:
a rolled sheet of flexible material having a first longitudinal edge, a second longitudinal edge, an outer surface, and a sheet surface between the first and second longitudinal edges that forms an inner shaft surface,
the first and second longitudinal edges of the sheet being joined in abutment to form a single seam extending along a length of the shaft,
the sheet surface including a plurality of longitudinal ribs such that the rolled sheet forms a plurality of lumens within the shaft with the ribs separating the plurality of lumens from one another;
a plurality of holes;
a plurality of elongated members, each of the plurality of members extending within each of the plurality of lumens and including a conductor; and
an electrode;
wherein all or a portion of the first longitudinal edge joins to the second longitudinal edge;
each of the plurality of ribs include a base and a peak, the base of each spaced apart from one another and each rib joined to one another in proximity to their peaks;
the inner surface and the outer surface of the shaft form a wall;
the plurality of holes, formed through the wall, provide communication between one or more of the plurality of lumens and an area in proximity to the outer surface of the shaft; and
the electrode, formed about the outer surface of the shaft, couples to the conductor at a first location via a first hole of the plurality of holes.

20. A method for making a shaft included in a medical device, the method comprising:
forming a flexible sheet comprising a first longitudinal edge, a second longitudinal edge, an inner surface, and an outer surface, each extending along a length of the sheet the inner surface including a plurality of longitudinal ribs disposed in between, and substantially parallel to the first and second longitudinal edges;
disposing a plurality of elongated members on the inner surface, each of the plurality of members alongside one of the plurality of ribs such that the plurality of elongated members extends in a direction substantially parallel to the plurality of ribs; and
rolling the sheet to form the shaft such that the first longitudinal edge and the second longitudinal edge come approximately together and the inner surface forms a plurality of lumens, the plurality of lumens separated from one another by the plurality of ribs and each of the plurality of elongated members extending within one of the plurality of lumens.

21. The method of claim 20, further comprising joining all or a portion of the first longitudinal edge to all or a portion of the second longitudinal edge.

22. The method of claim 20, further comprising forming a plurality of holes communicating between the inner surface and the outer surface, each of the plurality of holes being disposed between each of the plurality of ribs.

23. The method of claim 22, wherein one of the plurality of elongated members includes a conductor and further comprising coupling an electrode, formed about the outer surface, to the conductor via one of the plurality of holes.

24. The method of claim 22, wherein one of the plurality of elongated members includes a conductor and further comprising coupling an electrode, formed about the outer surface, to the conductor via two of the plurality of holes.

25. The method of claim 21, wherein means for joining all or a portion of the first longitudinal edge to all or a portion of the second longitudinal edge is selected from the group comprising adhesive bonding, solvent welding, and material re-flow.

26. The method of claim 20, further comprising assembling an outer sheath about an outer surface of the rolled shaft.

27. The method of claim 26, wherein assembling the outer sheath results in an interference fit of the sheath about the outer surface of the shaft.

28. The method of claim 20, wherein rolling the sheet further includes rolling about a central core.

29. The method of claim 20, further comprising applying an adhesive to the plurality of ribs to join the ribs together when the sheet is rolled to form the shaft.

30. A medical device comprising a shaft, the shaft comprising:
- a rolled sheet of flexible material having a first longitudinal edge, a second longitudinal edge, an outer surface, and a sheet surface between the first and second longitudinal edges that forms an inner shaft surface,
- the first and second longitudinal edges of the sheet being joined in abutment to form a single seam extending along a length of the shaft,
- the sheet surface including a plurality of longitudinal ribs such that the rolled sheet forms a plurality of lumens within the shaft with the ribs separating the plurality of lumens from one another;
- one or two elongated members, at least one of the members extending within one of the lumens; and
- the rib includes a peak, the peak joined in proximity to the seam.

* * * * *